United States Patent [19]

Giraudon et al.

[11] Patent Number: 4,536,502
[45] Date of Patent: Aug. 20, 1985

[54] FUNGICIDAL 2-CYANOBENZIMIDAZOLE DERIVATIVES, COMPOSITIONS, AND METHOD OF USE

[75] Inventors: Raymond Giraudon, Lesigny; Georges Santini, Thiais, both of France

[73] Assignee: Rhone-Poulenc Agrochimie, Lyons, France

[21] Appl. No.: 463,055

[22] Filed: Feb. 1, 1983

[30] Foreign Application Priority Data

Feb. 9, 1982 [FR] France .................. 82 02281

[51] Int. Cl.³ .............. A01N 43/32; A01N 43/52; C07D 413/02; C07D 235/04
[52] U.S. Cl. ........................ 514/227; 514/395; 544/139; 548/327; 548/329
[58] Field of Search ............ 548/329, 325, 326, 327, 548/330, 331, 332, 333; 544/159, 139; 424/273 B, 248.4

[56] References Cited

U.S. PATENT DOCUMENTS

| | | | |
|---|---|---|---|
| 3,576,818 | 4/1971 | Samuel et al. | 548/331 |
| 3,849,431 | 11/1974 | Gallay et al. | 548/331 |
| 3,853,908 | 12/1974 | Widdig et al. | 424/248 |
| 3,920,681 | 11/1975 | Buchel et al. | 424/273 |
| 4,018,790 | 4/1977 | Paget et al. | 424/267 |
| 4,118,742 | 10/1978 | Paget et al. | 548/306 |
| 4,122,184 | 10/1978 | Soper | 424/273 |
| 4,174,454 | 11/1979 | Paget et al. | 548/306 |
| 4,230,868 | 10/1980 | Paget et al. | 548/306 |
| 4,289,782 | 9/1981 | Paget et al. | 424/273 B |
| 4,338,329 | 7/1982 | Paget et al. | 424/270 |

FOREIGN PATENT DOCUMENTS

| | | | |
|---|---|---|---|
| 1450505 | 10/1966 | France | 548/331 |
| 2051493 | 5/1971 | France | 548/331 |
| 2070090 | 9/1971 | France | 548/331 |
| 7004376 | 10/1970 | Netherlands | 548/331 |

OTHER PUBLICATIONS

Merck Index of Classic Chemical Reactions, Ninth Ed., P ONR-44, ISBN 911910-26-3.
Chemical Abstracts, vol. #96, Article 6300X, (Wikel et al.).

Primary Examiner—Henry R. Jiles
Assistant Examiner—J. G. Mullins
Attorney, Agent, or Firm—Burns, Doane, Swecker & Mathis

[57] ABSTRACT

The invention relates to new 2-cyanobenzimidazole derivatives.

These compounds correspond to the formula (I):

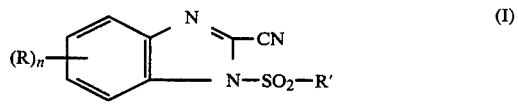

in which:

n is 0, 1, 2 or 3,

R is halogen; optionally halogen-substituted lower alkyl or alkylthio; lower alkoxy optionally substituted by one or more halogens or by the phenyl radical; lower alkenyl; lower alkynyl; amino optionally substituted by one or two alkyls; $NO_2$—; CN—; CNO—; NCS—; , SCN—; lower alkylsulphonyl; sulphamoyl optionally substituted by one or two alkyls; lower alkylsulphinyl; optionally substituted acyl; or alkoxycarbonyl, and R' is optionally halogen-substituted lower alkyl, amino optionally substituted by one or two alkyl radicals, or a nitrogen atom substituted by two radicals forming a heterorcyclic ring with this nitrogen atom, the heterocyclic ring containing from 4 to 6 ring members and from 1 to 3 hetero-atoms in the ring.

They can be used in agriculture, in particular for combating phytopathogenic fungi and for combating mites.

6 Claims, No Drawings

FUNGICIDAL 2-CYANOBENZIMIDAZOLE DERIVATIVES, COMPOSITIONS, AND METHOD OF USE

The present patent application relates to new 2-cyanobenzimidazole derivatives and also to the preparation of these compounds. It furthermore relates to the pesticidal compositions, especially antifungal and acaricidal compositions, which can be used in agriculture and which contain one of these compounds as the active ingredient, and also to the pesticidal treatments, and more particularly the antifungal and acaricidal treatments, carried out using these compounds.

U.S. Pat. No. 3,576,818 describes 2-cyanobenzimidazole derivatives corresponding to the formula (I)

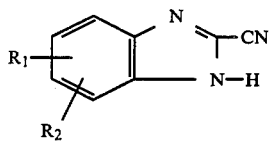

in which $R_1$ and $R_2$ are chosen from the group comprising hydrogen, chlorine, bromine, $NO_2$ and alkyl and alkoxy radicals containing at most 4 carbon atoms. This U.S. patent indicates that these compounds (I) can be used as bactericides and antiseptics; Example No. 1 of the said patent describes 2-cyanobenzimidazole, i.e. the compound according to the formula (I) in which $R_1$ and $R_2$ represent the hydrogen atom.

French Patent Application No. 2,051,493 describes 2-cyanobenzimidazole derivatives in which the nitrogen atom in the 1-position on the benzimidazole ring can be substituted by a hydrogen atom or an alkyl or alkoxycarbonyl radical. It indicates that these compounds have a biocidal activity and can be used a fungicides, anthelmintics, insecticides and herbicides. Example No. 4 of the said French Patent Application describes 2-cyanobenzimidazole, which has already been mentioned above.

French Patent Application No. 2,070,090 describes 2-cyanobenzimidazole derivatives in which the nitrogen atom in the 1-position on the benzimidazole ring can be substituted by the hydrogen atom or an alkyl, alkoxyalkyl, alkenyl, carboxyalkyl, alkanoyl, aminoalkyl, hydroxyl, alkoxy, carboxyalkoxy, sulphoalkoxy or aminoalkoxy radical, and teaches that these compounds can be used as anthelmintics, as anticoccidial agents and as pesticides, e.g. herbicides and bactericides.

The present patent application relates to 2-cyanobenzimidazole derivatives which are different from those described in the abovementioned documents and which possess noteworthy antifungal properties. Some of these new compounds furthermore possess valuable acaricidal properties.

The new 2-cyanobenzimidazole derivatives according to the invention are characterised in that they correspond to the general formula (II):

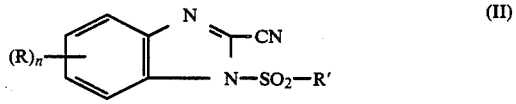

in which n, R and R' have the meanings indicated below, it being understood that, hereafter, the adjective "lower" applied to an organic radical means that this radical contains at most six carbon atoms, unless stated otherwise.

In the formula (II):

n represents an integer which can be equal to 0, 1, 2 or 3;

R represents a halogen atom (preferably a chlorine, fluorine or bromine atom) or a lower alkyl radical optionally substituted by one or more halogen atoms (such as e.g. the methyl radical or the trifluoromethyl radical); a lower alkoxy radical optionally substituted by one or more halogen atoms or by the phenyl radical (such as e.g. the methoxy radical, the trifluoromethoxy radical or the benzyloxy radical); a lower alkylthio radical optionally substituted by one or more halogen atoms; a lower alkenyl radical; a lower alkynyl radical; an amino radical optionally substituted by one or two identical or different lower alkyl radicals; a nitro radical; a cyano radical; a cyanato radical (CNO—); a thiocyanato radical (NCS—); an isothiocyanato radical (SCN—); a lower alkylsulphonyl radical; a sulphamoyl radical optionally substituted by one or two identical or different lower alkyl radicals; a lower alkylsulphinyl radical; an acyl radical optionally substituted by one or more halogen atoms (e.g. optionally halogen-substituted lower alkanoyl or optionally halogen-substituted benzoyl); or an alkoxycarbonyl radical containing from 2 to 5 carbon atoms (e.g. methoxycarbonyl), it being understood that if n is greater than or equal to 2, the substituents R can be either identical or different; and R' represents a lower alkyl or cycloalkyl radical optionally substituted by one or more halogen atoms (such as e.g. the methyl, ethyl, isopropyl or trichloromethyl radical or the like); an amino radical optionally substituted by one or two identical or different lower alkyl radicals which are themselves optionally substituted; or a nitrogen atom substituted by two radicals forming a heterocyclic ring with this nitrogen atom, the heterocyclic ring itself being optionally substituted and containing from 4 to 6 ring members and from 1 to 3 heteroatoms in the ring (such as e.g. the morpholino radical, the pyrrolidino radical or the like).

In terms of the present text, it will be understood that the alkyl radicals or portions can be either linear or branched. The same applies to the alkenyl and alkynyl radicals.

Amongst the compounds corresponding to the general formula (II), a sub-family which is preferred because of its noteworthy antifungal properties consists of the compounds according to the formula (II) in which:

n and R have the same meaning as above, and

R' represents the dimethylamino radical, an alkyl radical containing from 1 to 3 carbon atoms and optionally substituted by one or more halogens, or a nitrogen atom substituted by two radicals forming a heterocyclic ring with this nitrogen atom, the heterocyclic ring containing from 4 to 6 ring members and optionally containing the oxygen atom as a second heterocyclic atom in the ring (i.e. in addition to the nitrogen atom).

Amongst these preferred antifungal compounds, a preferred sub-family consists of the compounds corresponding to the formula (II) in which:

n has the same meaning as above,

R represents a halogen atom or an alkyl radical containing from 1 to 3 carbon atoms; a trifluoromethyl radical; an optionally halogen-substituted alkoxy radical containing from 1 to 3 carbon atoms; an amino radical; a nitro radical; a cyano radical; or an alkylsulphonyl radical containing from 1 to 3 carbon atoms, it being possible for the substituents R to be either identical or different, and R' represents the dimethylamino radical, an alkyl radical containing from 1 to 3 carbon atoms (advantageously the isopropyl radical), the pyrrolidino radical or the morpholino radical.

Amongst the compounds corresponding to the general formula (II), it has been observed that those in which n is equal to one, two or three, and at least one of the substituents R represents the trifluoromethyl radical possess a valuable acaricidal activity, especially towards plant-eating mites, in addition to their antifungal properties.

The invention furthermore relates to a process for the preparation of the compounds according to the formula (II).

This process consists in reacting a 2-cyanobenzimidazole of the formula (III)

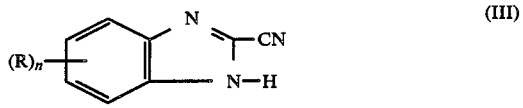

in which R and n have the same meaning as in the formula (II), or an alkali metal salt or ammonium salt of this 2-cyanobenzimidazole (III), with a halide of the formula (IV)

$$X-SO_2R'$$ (IV)

in which R' has the same meaning as in the formula (II) and X represents a halogen atom, preferably a chlorine atom.

The reaction of the 2-cyanobenzimidazole (III) with the halide (IV) is advantageously carried out in the presence of an acid acceptor, in an anhydrous or non-anhydrous medium, in a solvent which is inert under the reaction conditions, generally at the b.p. of the solvent. Acid acceptors which may be mentioned are inorganic bases such as e.g. sodium hydroxide or potassium hydroxide and alkali metal or alkaline earth metal carbonates, and nitrogen-containing bases such as triethylamine. The solvents used are advantageously polar aprotic solvents such as e.g. dimethylformamide, dimethylacetamide, dimethyl sulphoxide, acetone, methyl ethyl ketone, acetonitrile or N-methylpyrrolidone. If desired, this reaction can be carried out in the presence of a suitable catalyst. Phase transfer catalysts, such as e.g. quaternary ammonium derivatives, may be mentioned as catalysts which can be used.

The reaction of the alkali metal salt or ammonium salt of the 2-cyanobenzimidazole (III) with the halide (IV) does not require the presence of an acid acceptor. It is carried out in an anhydrous or non-anhydrous medium, in a solvent which is inert under the reaction conditions, generally at the b.p. of the solvent. The polar aprotic solvents mentioned above can advantageously be used in this reaction.

If desired, this reaction can be carried out in the presence of a suitable catalyst such as e.g. a phase transfer catalyst (e.g. a quaternary ammonium derivative).

The alkali metal salt or ammonium salt of the compound (III) is prepared in a prior operation, if appropriate carried out in situ, by reacting a suitable base (e.g. sodium hydroxide, potassium hydroxide or ammonia), an alkali metal carbonate or an alkali metal alcoholate (e.g. sodium methylate or sodium or potassium ethylate) with this compound (III).

At the end of the reaction, irrespective of the process used, the compound formed is isolated from the reaction medium by any means which is in itself known, such as e.g. by distillation of the solvent, by crystallisation of the product from the reaction medium or by filtration, and then, if necessary, this compound is purified by customary methods such as recrystallisation from a suitable solvent.

The 2-cyanobenzimidazole of the formula (III) used as the starting material can be prepared according to one or other of the methods A, B and C described below:

Method A:

Reaction of ammonia with a 2-trihalogenomethyl-cyanobenzimidazole by the process described in U.S. Pat. No. 3,576,818 mentioned above.

Method B:

Reaction of phosphorus trichloride with a 2-cyano-1-hydroxybenzimidazole of the formula (V)

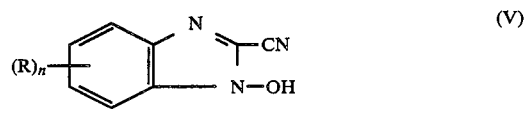

in which R and n have the same meaning as in the formula (II), the reaction being carried out in acetone heated to the reflux temperature.

The 2-cyano-1-hydroxybenzimidazole (V) can be obtained from the 2-(2-nitrophenyl)-aminoacetonitrile of the formula (VI)

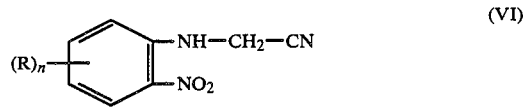

in which R and n have the same meaning as above, by heating in the presence of potassium carbonate, according to the method described by L. KONOPSKI and B. SERAFIN in Rocz. Chem. 51, 1873 (1977).

The compound (VI) can be obtained from the corresponding 2-nitroaniline, the reaction being carried out according to the method described by K. DINROTH and H. C. AURICH in Chem. Ber. 98,3902 (1965).

Method C:

Reaction of a dehydrating agent, such as POCl$_3$ or SOCl$_2$, with the 2-hydroxyiminomethylbenzimidazole of the formula (VII)

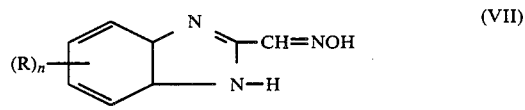

in which R and n have the same meaning as in the formula (II).

The examples below, which are described without implying a limitation, illustrate the preparation of the compounds according to the invention and their use as fungicides and acaricides. The structures of the compounds described in these examples were confirmed by nuclear magnetic resonance spectrometry (NMR) and/or by infrared spectrometry.

EXAMPLE 1

Preparation of 1-dimethylsulphamoyl-2-cyanobenzimidazole (compound 1) of the formula

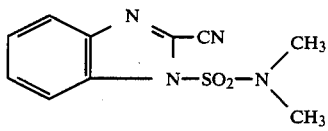
(Compound 1)

Anhydrous potassium carbonate (4.83 g), and then N,N-dimethylsulphamoyl chloride (7 ml) and tetrabutylammonium hydrogensulphate (1.18 g), are added to a solution of 2-cyanobenzimidazole (10 g) in acetonitrile (100 ml).

The mixture is then heated under reflux for 3 hours. After cooling to about 25° C., ethyl acetate (300 ml) is added. The reaction mixture is then filtered and the filtrate is concentrated under reduced pressure (0.032 bar). The solid obtained is recrystallised from isopropyl ether (200 ml).

This gives 1-dimethylsulphamoyl-2-cyanobenzimidazole (5.3 g; yield: 30.3%) melting at 93° C.:

|  | Elementary Composition | | | | |
|---|---|---|---|---|---|
|  | C | H | N | O | S |
| % calculated | 47.99 | 4.03 | 22.38 | 12.78 | 12.81 |
| % found | 48.31 | 4.10 | 22.46 | 12.27 | 13.00 |

The 2-cyanobenzimidazole used as the starting material was obtained by reacting ammonia with 2-trichloromethylbenzimidazole according to the method described in Example No. 1 of U.S. Pat. No. 3,576,818.

2-Cyanobenzimidazole was also prepared as indicated below:

2-Hydroxyiminomethylbenzimidazole (79 g) is added in the course of one hour to sulphinyl chloride (300 ml); the addition is exothermic and causes the evolution of gas. The reaction mixture is heated for a further two hours 30 minutes under reflux and then, after cooling, diluted with petroleum ether (200 ml). The precipitate obtained is filtered off and then washed with a solution of potassium carbonate.

After recrystallisation from a mixture of acetonitrile/ethyl acetate, 2-cyanobenzimidazole (42.5 g; 60.6%) is obtained, which melts at 268°.

EXAMPLE 2

Preparation of 1-dimethylsulphamoyl-2-cyanobenz-5-chlorobenzimidazole (compound 2A) and of 1-dimethylsulphamoyl-2-cyano-6-chlorobenzimidazole (compound 2B)

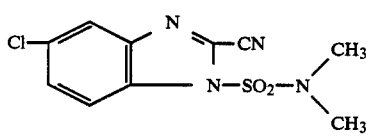
Compound 2A

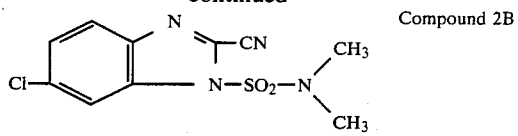
Compound 2B

Potassium hydroxide flakes (2.87 g) are added to a suspension of 2-cyano-5-chlorobenzimidazole (8 g) in acetone (100 ml) dried over $K_2CO_3$.

After about 30 minutes, the potassium hydroxide has dissolved and the reaction mixture has become virtually homogeneous.

Dimethylsulphamoyl chloride (4.85 ml) is then added all at once and the reaction mixture is stirred for 18 hours. This reaction mixture is subsequently filtered and the filtrate is then concentrated under reduced pressure (0.026 bar) at about 50° C. This gives a pinkish-white solid, which is recrystallised from isopropanol (150 ml) to give a white solid (6.5 g) melting at 130° C.

From analysis by NMR and infrared spectrography, this compound is found to be a mixture of substantially equal proportions of 1-dimethylsulphamoyl-2-cyano-5-chlorobenzimidazole and 1-dimethylsulphamoyl-2-cyano-6-chlorobenzimidazole, this mixture of isomers having the elementary composition below:

|  | C | H | Cl | N | O | S |
|---|---|---|---|---|---|---|
| % calculated | 42.18 | 3.18 | 12.45 | 19.68 | 11.24 | 11.26 |
| % found | 42.28 | 3.18 | 12.41 | 19.42 | 11.27 | 11.20 |

These two isomers are then separated by chromatography on silica under slight pressure (flash chromatography) and 1-dimethylsulphamoyl-2-cyano-5-chlorobenzimidazole (compound 2A) and 1-dimethylsulphamoyl-2-cyano-6-chlorobenzimidazole (compound 2B) are thus obtained separately. One of these compounds melts at 147° C. and the other at 167° C.

EXAMPLE 3

Preparation of 1-isopropylsulphonyl-2-cyano-5-trifluoromethylbenzimidazole (compound 3A) and 1-isopropylsulphonyl-2-cyano-6-trifluoro-methylbenzimidazole (compound 3B)

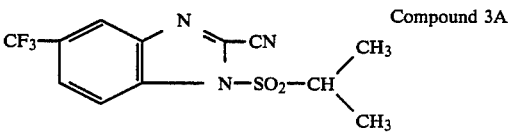
Compound 3A

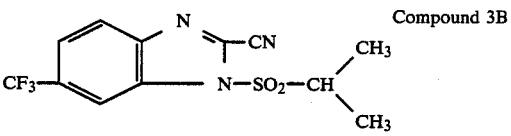
Compound 3B

Potassium hydroxide flakes (3.62 g) are added to a solution of 2-cyano-5-trifluoromethylbenzimidazole (12 g) in acetone (100 ml).

After stirring for 15 minutes at 25° C., isopropylsulphonyl chloride (6.35 ml) is added. The mixture is subsequently kept at the reflux temperature of the solvent for two hours and then concentrated, after cooling. The solid residue obtained is dissolved in methylene chloride (250 ml) and the solution obtained is washed with distilled water (2×200 ml). After drying, the methylene chloride solution is concentrated and the residue obtained is then recrystallised from isopropanol (50 ml). This gives a white solid (11.2 g; yield: 61.9%) melting at 120° C.

From NMR and infrared spectrography, this compound is found to be a mixture of substantially equal proportions of 1-isopropylsulphonyl-2-cyano-5-trifluoromethylbenzimidazole (compound 3A) and 1-isopropylsulphonyl-2-cyano-6-trifluoromethylbenzimidazole (compound 3B), this mixture of isomers having the elementary composition below:

|  | C | H | F | N | S |
|---|---|---|---|---|---|
| % calculated | 45.42 | 3.18 | 17.96 | 13.24 | 10.10 |
| % found | 45.56 | 3.03 | 17.93 | 13.07 | 10.07 |

EXAMPLE 4

Preparation of
1-methylsulphonyl-2-cyano-5-trifluoromethylbenzimidazole (compound 4A) and
1-methylsulphonyl-2-cyano-6-trifluoromethyl-benzimidazole (compound 4B)

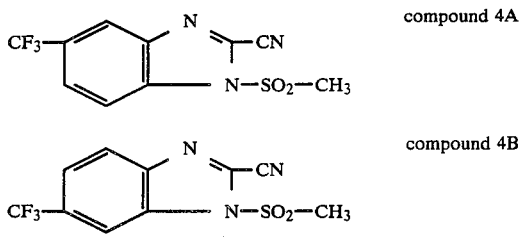

The method described in Example No. 3 is followed, using the appropriate starting materials, except that the recrystallisation solvent is toluene (instead of isopropanol).

This gives a mixture (78/22) of compounds 4A and 4B.

M.p. of the mixture: 142° C.
Elementary composition of the mixture:

|  | C | N | N | S |
|---|---|---|---|---|
| % calculated | 41.52 | 2.09 | 14.53 | 11.08 |
| % found | 42.85 | 2.08 | 15.22 | 10.10 |

EXAMPLE 5

Preparation of
1-dimethylsulphamoyl-2-cyano-5-trifluoromethylbenzimidazole (compound 5A) and
1-dimethylsulphamoyl-2-cyana-6-trifluoromethyl-benzimidazole (compound 5B)

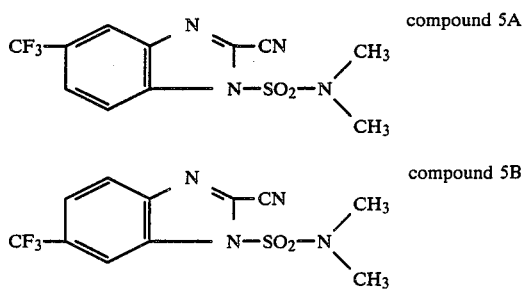

The method described in Example 3 is followed, using the appropriate starting materials.

This gives a mixture of substantially equal proportions of compounds 5A and 5B.

M.p. of the mixture: 120° C.
Elementary composition of the mixture:

|  | C | H | F | N | O | S |
|---|---|---|---|---|---|---|
| % calculated | 41.51 | 2.85 | 17.91 | 12.60 | 10.05 | 10.07 |
| % found | 41.53 | 2.75 | 17.87 | 12.12 | 11.50 | 10.14 |

EXAMPLE 6

Compounds Nos. 6A to 71 were prepared following one or other of the methods described in Examples 1 and 3, using the appropriate starting materials. The formulae and m.p. of these compounds or their mixtures, and also of the compounds or mixtures of compounds described in the above examples, are reported in the table below. In this table:

in the R column, the number indicated in brackets before the substituent indicates the position of the substituent on the benzimidazole ring;

in the R' column, the word "ditto" means that, for the compound in question, the radical R' has the same meaning as for the compound immediately preceding it in this table. This notation has been used systematically in the case where the isomers (A and B) in the mixture obtained differ from one another only by the position of the substituent or substituents R on the benzimidazole ring;

in the "m.p." column, the letter "M" means that the m.p. indicated is that of a mixture comprising the two compounds in the proportions by weight indicated after the letter M.

| N° | n | R | R' | M.p. |
|---|---|---|---|---|
| 1 | 0 |  | —N(CH₃)₂ | 93° C. |
| 2A | 1 | (5)-Cl | —N(CH₃)₂ | M 50/50: |
| 2B | 1 | (6)-Cl | —N(CH₃)₂ | 130° C. |
| 2A | 1 | (5)-Cl | —N(CH₃)₂ | 147° C. |
| 2B | 1 | (6)-Cl | —N(CH₃)₂ | 165° C. |

-continued

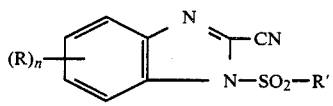

| N° | n | R | R' | M.p. |
|---|---|---|---|---|
| 3A | 1 | (5)-CF$_3$ | —CH(CH$_3$)$_2$ | M 50/50: |
| 3B | 1 | (6)-CF$_3$ | —CH(CH$_3$)$_2$ | 120° C. |
| 4A | 1 | (5)-CF$_3$ | CH$_3$ | M 78/22: |
| 4B | 1 | (6)-CF$_3$ | CH$_3$ | 142° C. |
| 5A | 1 | (5)-CF$_3$ | —N(CH$_3$)$_2$ | M 50/50: |
| 5B | 1 | (6)-CF$_3$ | —N(CH$_3$)$_2$ | 120° C. |
| 6A | 1 | (5)-CH$_3$ | —N(CH$_3$)$_2$ | M 50/50: |
| 6B | 1 | (6)-CH$_3$ | —N(CH$_3$)$_2$ | 110° C. |
| 7A | 1 | (5)-NO$_2$ | —N(CH$_3$)$_2$ | M 50/50: |
| 7B | 1 | (6)-NO$_2$ | —N(CH$_3$)$_2$ | 178° C. |
| 7A | 1 | (5)-NO$_2$ | —N(CH$_3$)$_2$ | 207° C. |
| 7B | 1 | (6)-NO$_2$ | —N(CH$_3$)$_2$ | 190° C. |
| 8 | 2 | (5)-CH$_3$, (6)-CH$_3$ | —N(CH$_3$)$_2$ | 149° C. |
| 9 | 2 | (4)-Cl, (6)-Cl | —N(CH$_3$)$_2$ | 177° C. |
| 10 | 1 | (4)-Cl | —N(CH$_3$)$_2$ | 130° C. |
| 11 | 1 | (5)-C(CH$_3$)$_3$ | —N(CH$_3$)$_2$ | 125° C. |
| 12A | 1 | (5)-CO—C$_6$H$_5$ | —N(CH$_3$)$_2$ | M 50/50: |
| 12B | 1 | (6)-CO—C$_6$H$_5$ | —N(CH$_3$)$_2$ | 132° C. |
| 13A | 1 | (5)-OCH$_3$ | —N(CH$_3$)$_2$ | M 50/50: |
| 13B | 1 | (6)-OCH$_3$ | —N(CH$_3$)$_2$ | 125° C. |
| 14 | 2 | (5)-Cl, (6)-Cl | —N(CH$_3$)$_2$ | 174° C. |
| 15A | 1 | (5)-F | —N(CH$_3$)$_2$ | M 50/50 |
| 15B | 1 | (6)-F | —N(CH$_3$)$_2$ | 109–110° C. |
| 16 | 0 |  | —CH$_3$ | 198° C. |
| 17 | 2 | (4)-Cl, (6)-Cl | —CH$_3$ | 204° C. |
| 18 | 1 | (4)-CH$_3$ | —CH$_3$ | 171° C. |
| 19A | 2 | (5)-Cl, (6)-CH$_3$ | —N(CH$_3$)$_2$ | M 43/57: |
| 19B | 2 | (5)-CH$_3$, (6)Cl | —N(CH$_3$)$_2$ | 181° C. |
| 20 | 1 | (4)-Cl | —CH$_3$ | 173° C. |
| 21 | 1 | (4)-Cl | —CH(CH$_3$)$_2$ | 120° C. |
| 22 | 0 |  | —CH(CH$_3$)$_2$ | 118° C. |
| 23 | 2 | (4)-Cl, (6)-Cl | —CH(CH$_3$)$_2$ | 176° C. |
| 24 | 2 | (5)-Cl, (6)-Cl | —CH(CH$_3$)$_2$ | 181° C. |
| 25A | 1 | (5)-Br | —N(CH$_3$)$_2$ | M 50/50 |
| 25B | 1 | (6)-Br | —N(CH$_3$)$_2$ | 138–142° C. |
| 26 | 1 | (4)-Br | —N(CH$_3$)$_2$ | 143° C. |
| 27 | 2 | (4)-NO$_2$, (5)-OCH$_3$ | —N(CH$_3$)$_2$ | 185° C. |
| 28 | 3 | (4)-NO$_2$, (5)-OCH$_3$ (6)-OCH$_3$ | —N(CH$_3$)$_2$ | 180° C. |
| 29A | 1 | (5)-CN | —N(CH$_3$)$_2$ | M 43/57 |
| 29B | 1 | (6)-CN | —N(CH$_3$)$_2$ | 160° C. to 220° C. |
| 30A | 1 | (5)-Cl | —N(CH$_3$)(C$_2$H$_5$) | M 55/45: 91° C. |
| 30B | 1 | (6)-Cl | —N(CH$_3$)(C$_2$H$_5$) |  |
| 31A | 1 | (5)-NO$_2$ | —CH(CH$_3$)$_2$ | M 64/36: |
| 31B | 1 | (6)-NO$_2$ | —CH(CH$_3$)$_2$ | 150° C. |
| 32A | 1 | (5)-Cl | —CH(CH$_3$)$_2$ | M 30/70: |
| 32B | 1 | (6)-Cl | —CH(CH$_3$)$_2$ | 120° C. |
| 33A | 1 | (5)-O—CH$_2$—C$_6$H$_5$ | —CH(CH$_3$)$_2$ | M(40/60 or 60/40): |
| 33B | 1 | (6)-O—CH$_2$—C$_6$H$_5$ | —CH(CH$_3$)$_2$ | 135° C. |
| 34A | 1 | (5)-O—CH$_2$—C$_6$H$_5$ | —N(CH$_3$)$_2$ | M(50/50): |
| 34B | 1 | (6)-O—CH$_2$—C$_6$H$_5$ | —N(CH$_3$)$_2$ | 120° C. |
| 35A | 1 | (5)-F | —N(CH$_3$)(C$_2$H$_5$) | M 50/50: 96° C. |
| 35B | 1 | (6)-F | —N(CH$_3$)(C$_2$H$_5$) |  |
| 36A | 1 | (5)-SCH$_3$ | —N(CH$_3$)$_2$ | M 50/50: |

-continued

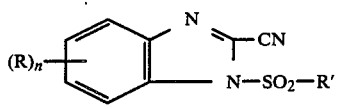

| N° | n | R | R' | M.p. |
|---|---|---|---|---|
| 36B | 1 | (6)-SCH₃ | —N(CH₃)₂ | 108° C. |
| 37A | 2 | (5)-Cl, (6)-OCH₃ | —N(CH₃)₂ | M 50/50 |
| 37B | 2 | (5)-OCH₃, (6)-Cl | —N(CH₃)₂ | 190° C. and 205° C. |
| 38 | 1 | (5)- or (6)-NH₂ | —N(CH₃)₂ | 212° C. |
| 39 | 2 | (4)-Br, (6)-Br | —N(CH₃)₂ | 215° C. |
| 40A | 2 | (5)-NO₂, (6)-Cl | —N(CH₃)₂ | M 50/50: |
| 40B | 2 | (5)-Cl, (6)-NO₂ | —N(CH₃)₂ | 184° C. |
| 41A | 2 | (5)-Cl, (6)-SO₂CH₃ | —N(CH₃)₂ | M 50/50: |
| 41B | 2 | (5)-SO₂CH₃, (6)-Cl | —N(CH₃)₂ | 191° C. |
| 42 | 1 | (4)-NH₂ | —N(CH₃)₂ | 140–150° C. |
| 43 | 2 | (4)-CH₃, (6)-Br | —N(CH₃)₂ | 207° C. |
| 44 | 1 | (5)- or (6)-NCS | —N(CH₃)₂ | 118–120° C. |
| 45 | 2 | (4)-Cl, (5)-Cl | —N(CH₃)₂ | 194–195° C. |
| 46A | 1 | (5)-SO₂—NH₂ | —N(CH₃)₂ | M 50/50: |
| 46B | 1 | (6)-SO₂—NH₂ | —N(CH₃)₂ | 158° C. |
| 47 | 1 | (6)-NCS or (5)-NCS | —N(CH₃)₂ | 115–120° C. |
| 48 | 3 | (4)-Cl, (5)OCH₃ (6)-Cl | —N(CH₃)₂ | 160° C. |
| 49 | 1 | (4)-NO₂ | —N(CH₃)₂ | 196° C. |
| 50 | 2 | (4)-CH₃, (5)-Cl | —N(CH₃)₂ | 154° C. |
| 51 | 3 | (3)-Cl, (4)-Cl, (5)-Cl | —N(CH₃)₂ | 208–210° C. |
| 52A | 1 | (5)-SO—CH₃ | —N(CH₃)₂ | M 63/37: |
| 52B | 1 | (6)-SO—CH₃ | —N(CH₃)₂ | 116° C. |
| 53A | 1 | (5)-SO₂—CH₃ | —N(CH₃)₂ | M 55/45: |
| 53B | 1 | (6)-SO₂—CH₃ | —N(CH₃)₂ | 166° C. |
| 54A | 1 | (5)-CF₃ | —CCl₃ | M 65/35: |
| 54B | 1 | (6)-CF₃ | —CCl₃ | 114–116° C. |
| 55 | 2 | (4)-CH₃, (6)-Cl | —N(CH₃)₂ | 185° C. |
| 56A | 2 | (5)-Cl, (6)-CF₃ | —N(CH₃)₂ | M 50/50: |
| 56B | 2 | (5)-CF₃, (6)-Cl | —N(CH₃)₂ | 158° C. |
| 57 | 2 | (4)-Cl, (6)-Cl | —N(CH₂—CH₂)(CH₂—CH₂) (pyrrolidinyl) | 180° C. |
| 58A | 1 | (5)-CF₃ | —N(CH₂—CH₂)(CH₂—CH₂) (pyrrolidinyl) | M 50/50 125 to 130° C. |
| 58B | 1 | (6)-CF₃ | —N(CH₂—CH₂)(CH₂—CH₂) (pyrrolidinyl) | |
| 59A | 1 | (5)-CF₃ | —N(CH₂—CH₂)(CH₂—CH₂)O (morpholinyl) | M 50/50 155 to 165° C. |
| 59B | 1 | (6)-CF₃ | —N(CH₂—CH₂)(CH₂—CH₂)O (morpholinyl) | |
| 60A | 2 | (5)-Cl, (6)-CF₃ | —CH(CH₃)₂ | M 66/34: |
| 60B | 2 | (5)-CF₃, (6)-Cl | —CH(CH₃)₂ | 161° C. |
| 61 | 2 | (4)-CF₃, (6)-Cl | —N(CH₃)₂ | 188° C. |
| 62A | 1 | (5)-CO—O—CH₃ | —N(CH₃)₂ | M 40/60: |
| 62B | 1 | (6)-CO—O—CH₃ | —N(CH₃)₂ | 132° C. |
| 63A | 2 | (4)-Br, (5)-Cl | —N(CH₃)₂ | M 50/50 |
| 63B | 2 | (4)-Cl, (5)-Br | —N(CH₃)₂ | 168–170° C. |
| 64 | 2 | (4)-CH₃, (5)-NO₂ | —N(CH₃)₂ | 194° C. |
| 65A | 2 | (5)-NO₂, (6)-CF₃ | —N(CH₃)₂ | M 60/40: |
| 65B | 2 | (5)-CF₃, (6)-NO₂ | —N(CH₃)₂ | 171° C. |
| 66 | 2 | (4)-Cl, (6)-Cl | —N(C₂H₅)₂ | 153° C. |
| 67 | 2 | (4)-NO₂, (5)-CH₃ | —N(CH₃)₂ | 173° C. |

-continued

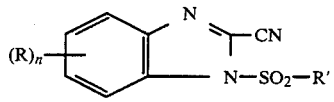

| N° | n | R | R' | M.p. |
|---|---|---|---|---|
| 68A | 2 | (5)-NO$_2$, (6)-CH$_3$ | —N(CH$_3$)$_2$ | M(65/35 or 35/65): |
| 68B | 2 | (5)-CH$_3$, (6)-NO$_2$ | —N(CH$_3$)$_2$ | 155° C. |
| 69 | 2 | (4)-Cl, (6)-F | —N(CH$_3$)$_2$ | 151° C. |
| 70 | 2 | (4)-CF$_3$, (6)-CF$_3$ | —N(CH$_3$)$_2$ | 160° C. |
| 71A | 1 | (5)-SCF$_3$ | —N(CH$_3$)$_2$ | M 80/20: |
| 71B | 1 | (6)-SCF$_3$ | —N(CH$_3$)$_2$ | 131° C. |

EXAMPLE 7

Greenhouse tests on tomato mildew

Tomato plants (*Lycopersicum esculentum*) of the Marmande variety are cultivated in pots. When these plants are one month old (5 to 6 leaf stage, height: 12 to 15 cm), they are treated by spraying with an aqueous suspension or solution of the substance to be tested, which has the desired concentration and contains 0.02% of a 20:1 ethylene oxide/sorbitan monooleate condensate. Each tomato plant is treated with about 5 ml of the solution or dispersion. For each concentration of active ingredient to be tested, the treatment is carried out on eight plants. Plants used as controls are treated with a solution not containing active ingredient, but containing 0.02% of the same ethylene oxide/sorbitan monooleate condensate.

After drying for 4 hours, each plant is contaminated by spraying with an aqueous suspension of spores of Phytophthora infestans, which is responsible for tomato mildew, at a rate of about 1 ml/plant (i.e. about $2.10^5$ spores per plant).

After this contamination, the tomato plants are incubated for three days at about 20° C. in an atmosphere saturated with humidity, and then for four days at about 17° C. under 70% to 80% relative humidity.

Seven days after the contamination, the results obtained in the case of the plants treated with the active ingredient to be tested are compared with those obtained in the case of the plants used as controls, and the minimum inhibitory concentration causing from 95 to 100% inhibition of the development of the fungus in question (MIC 95-100) is determined.

Under these conditions, it is observed that, for the compounds or mixtures of compounds described in the above examples, this concentration was respectively as follows:

| Compound or mixture tested | MIC (95-100) *Phytophthora infestans* in mg/liter |
|---|---|
| 1 | 62 |
| 2A | 4 |
| 2B | 4 |
| 2A + 2B | 4 |
| 3A + 3B | 8 |
| 4A + 4B | 31 |
| 5A + 5B | 2 |
| 6A + 6B | 62 |
| 7A + 7B | 2 |
| 7A | 2 |
| 7B | 2 |
| 9 | 4 |
| 10 | less than or equal to 4 |
| 12A + 12B | 125 |
| 13A + 13B | 250 |
| 14 | 4 |
| 15A + 15B | 31 |
| 16 | 31 |
| 18 | 125 |
| 19A + 19B | 62 |
| 20 | 250 |
| 21 | 16 |
| 22 | less than or equal to 250 |
| 23 | 8 |
| 24 | less than or equal to 31 |
| 25A + 25B | 31 |
| 26 | 8 |
| 27 | 15 |
| 29A + 29B | 4 |
| 30A + 30B | 250 |
| 31A + 31B | 16 |
| 32A + 32B | 31 |
| 36A + 36B | 125 |
| 40A + 40B | less than or equal to 125 |
| 41A + 41B | 16 |
| 42 | 500 |
| 44 | 250 |
| 48 | less than or equal to 125 |
| 49 | less than or equal to 4 |
| 51 | 8 |
| 52A + 52B | 125 |
| 53A + 53B | 31 |
| 55 | 250 |
| 56A + 56B | 1 |
| 57 | 8 |
| 58A + 58B | 16 |
| 59A + 59B | 31 |
| 60A + 60B | 4 |
| 61 | 1 |
| 63A + 63B | 4 |
| 64 | 8 |
| 65A + 65B | less than or equal to 4 |
| 66 | 500 |
| 67 | less than or equal to 500 |
| 68A + 68B | less than or equal to 4 |

In this experiment, the observed percentage inhibition of the development of the fungus in question was between 20% and 90%:

at a dose of 500 mg/liter for compounds Nos. 8, 11, 28, 43, 47 and 50 and for mixtures Nos. (35A+35B), (46A+46B), (62A+62B) and (54A+54B)

at a dose of 15 mg/liter for compounds Nos. 17, (33A+33B) and (37A+37B)

at a dose of 8 mg/liter for compound No. 39 at a dose of 4 mg/liter for compound No. 45.

The mixtures mentioned in this example and the example which follows are those whose composition by weight has been given in the table described above.

Comparison

2-Cyanobenzimidazole, described in the two documents mentioned above and tested under the same conditions, showed an MIC 95-100 of 2,000 mg/liter, which is therefore very much greater than that (62 mg/liter) of dimethylsulphamoyl-2-cyanobenzimidazole (compound 1 described above).

It is therefore observed, according to this test, that the replacement of the hydrogen atom located on the nitrogen in the 1-position on the ring by the dimethylsulphamoyl radical makes it possible to increase the antifungal activity considerably.

EXAMPLE 8

Greenhouse test on tobacco mildew

The procedure of the previous example is followed, except that the plants are tobacco plants (*Nicotiana tabacum*) of the Samson variety, and that these plants are contaminated with spores of *Peronospora tabacina*, which is responsible for tobacco mildew.

Under these conditions, it was observed that, for the compounds or mixtures of compounds described in the above examples, the minimum inhibitory concentrations causing from 95 to 100% inhibition of the fungus in question (MIC 95-100) are respectively as follows:

| Compound or mixture tested | MIC (95-100) *Peronospora tabaci* in mg/liter |
|---|---|
| 1 | 30 |
| 2A | 2 |
| 2B | 2 |
| 2A + 2B | 2 |
| 3A + 3B | 2 |
| 5A + 5B | 1 |
| 6A + 6B | greater than or equal to 62 |
| 7A + 7B | 2 |
| 7A | 4 |
| 7B | 4 |
| 9 | 2 |
| 10 | 62 |
| 11 | 62 |
| 13A + 13B | 125 |
| 14 | 1 |
| 15A + 15B | 4 |
| 18 | 62 |
| 19A + 19B | 15 |
| 21 | 16 |
| 23 | 8 |
| 24 | 31 |
| 25A + 25B | 1 |
| 26 | 31 |
| 27 | 125 |
| 29A + 29B | 2 |
| 30A + 30B | 125 |
| 36A + 36B | 500 |
| 39 | 62 |
| 40A + 40B | 16 |
| 45 | 500 |
| 48 | less than or equal to 500 |
| 49 | 16 |
| 50 | less than or equal to 125 |
| 51 | 32 |
| 52A + 52B | 500 |
| 55 | 62 |
| 56A + 56B | 1 |
| 58A + 58B | 16 |
| 59A + 59B | 500 |
| 60A + 60B | 2 |
| 61 | 8 |
| 62A + 62B | greater than or equal to 500 |
| 63A + 63B | 4 |
| 65A + 65B | 4 |
| 66 | 500 |
| 67 | less than or equal to 500 |

In this experiment, the observed percentage inhibition of the development of the fungus in question was between 20% and 90%:

at a dose of 500 mg/liter for compounds Nos. 38, 42 and 44 and for mixtures Nos. (31A+31B), 41A+41B), (53A+53B) and 28 at a dose of 15 mg/liter for compounds Nos. 16, 22, 57 and 64 and for mixtures Nos. (4A+4B), (12A+12B), (35A+35B), (37A+37B) and (54A+54B)

at a dose of 8 mg/liter for compound No. 21.

Comparison

2-Cyanobenzimidazole, described in the documents mentioned above and tested under the same conditions, did not show any antifungal activity at a dose of 1,000 mg/liter (% inhibition=0%).

Under the same conditions, 1-dimethylsulphamoyl-2-cyanobenzimidazole (compound No. 1) has a minimum inhibitory concentration (MIC 95-100) equal to 30 mg/liter.

EXAMPLE 9

Acaricidal activity by contact-ingestion (foliage treated by dipping: *Tetranychus urticae* koch, parthenogenetic females).

An aqueous emulsion of the active ingredient to be tested is prepared by grinding the latter, in a Potter mill, in water containing 0.02% of Tween 80. The aqueous emulsion is then brought to the desired concentration by dilution with water containing 0.01% of Scurol O.

Tween 80 is a 20:1 ethylene oxide/sorbitan monooleate condensate.

Scurol O is a 10:1 ethylene oxide/octylphenol condensate.

Bean plants (*Phaseolus vulgaris*—Contender variety) at the "cotyledonary leaf" stage are used. Each plant is treated by dipping the leaves for 10 seconds in the aqueous emulsion containing the active ingredient to be tested, at the desired concentration, two plants being used for each concentration. The experiment was carried out for active ingredient concentrations ranging from 2,000 mg/liter to 10 mg/liter. The bean plants are kept alive by immersing the roots and the base of the stem in distilled water.

After the surface of the foliage has dried, contamination is carried out by depositing, on each bean leaf, a highly contaminated leaf fragment produced by mite breeding. This leaf fragment is removed after 24 hours.

Three days after contamination, the number of dead mites and the number of living mites are counted under a binocular magnifying glass.

The percentage mortality is thus determined for each concentration (average of two experiments). These percentages are used to determine the concentration ($LC_{90}$) which causes 90% mortality of the mites. For the compounds or mixtures of compounds described above, this concentration is as follows:

| | |
|---|---|
| 3A + 3B | 26 mg/liter |
| 4A + 4B | 900 mg/liter |

|          |              |
| -------- | ------------ |
| 5A + 5B  | 70 mg/liter  |
| 56A + 56B | 30 mg/liter |
| 60A + 60B | 30 mg/liter |
| 61       | 2,000 mg/liter |
| 70       | 10 mg/liter  |
| 71A + 71B | 30 mg/liter |

Examples Nos. 7 and 8 described above illustrate the good antifungal activity of the compounds according to the invention. In another experiment, carried out on vines using mixtures Nos. 2A+2B and 7A+7B, it was observed that treatments carried out using spraying mixtures containing from 15 to 60 g/hl of one or other of these mixtures, and applied to the vine plants until dripping wet, provided a good protection against vine mildew (Plasmopara viticola).

Example No. 9 described above illustrates the good acaricidal activity, by contact-ingestion, of some of the compounds according to the invention. In another experiment, carried out on bean leaves contaminated with eggs of the same mite as in the said Example No. 9, it was observed that these same compounds had a good acaricidal/ovicidal activity by contact.

The compounds according to the invention are advantageously used as antifungal agents in the field of agriculture. They have a contact action and a systemic action and can be employed in a preventive and/or curative capacity for combating various phytopathogenic fungi such as e.g. numerous phycomycetes and basidiomycetes. As indicated above, some of these compounds can also be used advantageously as agents for combating mites, especially plant-eating mites.

For their use in practice, the compounds according to the invention are not generally employed by themselves. Most frequently, they are used in compositions which generally comprise, in addition to the active ingredient, an inert carrier (or diluent) and/or a surface-active agent which are compatible with the active ingredient.

These compositions also form part of the present invention. They usually contain from 0.001 to 95% by weight of active ingredient. Their content of surface-active agent is generally between 0% and 20% by weight.

In the present account, the term "carrier" denotes a natural or synthetic, organic or inorganic material with which the active ingredient is combined in order to facilitate its application to the plant, to seeds or to the soil. This carrier is therefore generally inert and it must be acceptable in agriculture, in particular to the plant treated. The carrier can be solid (clays, natural or synthetic silicates, silica, chalks, resins, waxes, solid fertilisers or the like) or liquid (water, alcohols, ketones, petroleum fractions, aromatic or paraffinic hydrocarbons, chlorohydrocarbons, liquefield gases or the like).

The surface-active agent can be an emulsifying, dispersing or wetting agent of ionic or non-ionic type. Examples which may be mentioned are salts of polyacrylic acids, salts of lignosulphonic acids, salts of phenolsulphonic or naphthalenesulphonic acids, polycondensates of ethylene oxide with fatty alcohols, fatty acids, fatty amines or substituted phenols (in particular alkyl phenols, arylphenols or styrylphenol), salts of sulphosuccinic acid esters, taurine derivatives (in particular alkyl-taurates) and phosphoric acid esters of condensates of ethylene oxide with alcohols or phenols. The presence of at least one surface-active agent is generally essential, especially if the inert carrier is insoluble in water and if the vehicle of application is water.

The compositions used in the invention can be in a fairly wide variety of solid or liquid forms.

As forms of solid compositions, there may be mentioned dusting powders (with an active ingredient content which can range up to 100%).

As forms of liquid compositions or compositions which are to be made up into liquid compositions on application, there may be mentioned solutions, in particular water-soluble concentrates, emulsifiable concentrates, emulsions, suspension concentrates, aerosols, wettable powders (or spraying powders) and pastes.

The emulsifiable or soluble concentrates most frequently comprise 10 to 80% of active ingredient, and the emulsions or solutions which are ready for application contain 0.001 to 20% of active ingredient. In addition to the solvent, and where necessary, the emulsifiable concentrates can contain a suitable co-solvent and from 2 to 20% of suitable additives such as stabilisers, surface-active agents, in particular emulsifying agents, penetrating agents, corrosion inhibitors, dyestuffs and adhesives.

Starting from these concentrates, emulsions of any desired concentration, which are particularly suitable for application to the crops, can be obtained by dilution with water.

The suspension concentrates, which can also be applied by spraying, are prepared so as to give a stable fluid product which does not form a deposit, and they usually contain from 10 to 75% of active ingredients, from 0.5 to 15% of surface-active agents, from 0.1 to 10% of thixotropic agents, from 0 to 10% of suitable additives such as anti-foam agents, corrosion inhibitors, stabilisers, penetrating agents and adhesives, and, as the carrier, water or an organic liquid in which the active ingredient is sparingly soluble or insoluble; certain organic solids, or inorganic salts, can be dissolved in the carrier in order to assist in preventing sedimentation or to act as anti-freeze agents for the water.

The wettable powders (or spraying powders) are usually prepared so as to contain 20 to 95% of active ingredients, and they usually contain, in addition to the solid carrier, from 0 to 5% of a wetting agent, from 3 to 10% of a dispersing agent and, where necessary, from 0 to 10% of one or more stabilisers and/or other additives such as penetrating agents, adhesives, anticaking agents, dyestuffs or the like.

The composition of a 50% strength wettable powder is now given as an example:

|                                                      |       |
| ---------------------------------------------------- | ----- |
| active ingredient (50/50 mixture of compounds 2A and 2B) | 50%   |
| ethylene oxide/fatty alcohol condensate (wetting agent) | 2.5%  |
| ethylene oxide/styrylphenol condensate (dispersing agent) | 5%    |
| chalk (inert carrier)                                | 42.5% |

Another example of a wettable powder has the following composition:

|                                                      |     |
| ---------------------------------------------------- | --- |
| active ingredient (50/50 mixture of compounds 5A and 5B) | 90% |
| ethylene oxide/fatty alcohol condensate (wetting agent) | 4%  |
| ethylene oxide/styrylphenol                          | 6%  |

-continued

| | |
|---|---|
| condensate (dispersing agent) | |

Another example of a 50% strength wettable powder has the following composition:

| | |
|---|---|
| active ingredient (50/50 mixture of compounds 7A and 7B) | 50% |
| mixture of anionic and non-ionic surface-active agents (wetting agent) | 2.5% |
| neutral sodium lignosulphonate (dispersing agent) | 5% |
| kaolin clay (inert carrier) | 42.5% |

This last composition was used in the case of the abovementioned treatments on vines.

To obtain these spraying powders or wettable powders, the active ingredient is intimately mixed with the additional substances in suitable mixers, and the mixture is ground in mills or other suitable grinders. This gives spraying powders of advantageous wettability and suspendability; they can be suspended in water at any desired concentration, and this suspension can be used very advantageously, in particular for application to the leaves of the plants.

As already stated, the aqueous dispersions and aqueous emulsions, e.g. compositions obtained by diluting, with water, a wettable powder or an emulsifiable concentrate according to the invention, are included in the general scope of the compositions which can be used in the present invention. The emulsions can be of the water-in-oil or oil-in-water type and they can have a thick consistency such as that of a "mayonnaise".

The granules, which are intended to be placed on the soil, are usually prepared so as to have dimensions of between 0.1 and 2 mm, and they can be manufactured by agglomeration or impregnation. In general, the granules contain 0.5 to 25% of active ingredient and 0 to 10% of additives such as stabilisers, slow-release modifiers, binders and solvents.

The compounds of the formula (II) can also be used in the form of dusting powders; thus, it is possible to use a composition comprising active ingredient (50 g) and talc (950 g); it is also possible to use a composition comprising active ingredient (20 g), finely divided silica (10 g) and talc (970 g); these constituents are mixed and ground and the mixture is applied by dusting.

The invention also relates to a process for the treatment of plants to combat phytopathogenic fungi.

This process consists in applying, to these plants, an effective amount of a composition containing a compound according to the formula (II) as the active ingredient. The expression "active amount" is understood as meaning an amount sufficient to enable the fungi present on these plants to be controlled and destroyed. The use doses can vary within wide limits, however, according to the fungus to be combated, the type of crop, the climatic conditions and the compound used.

In practice, doses ranging from 5 g/hl to 100 g/hl, essentially corresponding to doses of active ingredient per hectare of 50 g/ha to 1,000 g/ha, approximately, generally give good results.

Finally, the invention relates to a process for the treatment of plants to combat plant-eating mites, in which an effective amount of a composition containing an acaricidal compound corresponding to the formula (II) as the active ingredient is applied to these plants. In practice, doses ranging from 10 to 100 g/hl, approximately, generally give good results.

We claim:

1. A 2-cyanobenzimidazole derivative of the general formula:

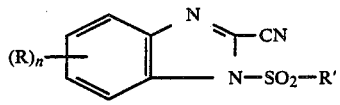

in which n represents an integer equal to 0, 1, 2 or 3;

R represents a halogen atom or a lower alkyl radical optionally substituted by one or more halogen atoms; a lower alkoxy radical optionally substituted by one or more halogen atoms or by the phenyl radical; a lower alkylthio radical optionally substituted by one or more halogen atoms; a lower alkenyl radical; a lower alkynyl radical; an amino radical optionally substituted by one or two identical or different lower alkyl radicals; a nitro radical; a cyano radical; a cyanato radical; a thiocyanato radical; an isothiocyanato radical; a lower alkylsulphonyl radical; a sulphamoyl radical optionally substituted by one or two identical or different lower alkyl radicals; a lower alkylsulphinyl radical; a lower alkanoyl radical optionally halogen substituted or a benzoyl radical optionally halogen substituted; or an alkoxycarbonyl radical containing from 2 to 5 carbon atoms, it being understood that if n is greater than or equal to 2, the substituents R can be either identical or different; and R' represents a lower alkyl or cycloalkyl radical optionally substituted by one or more halogen atoms; an amino radical optionally substituted by one or two identical or different lower alkyl radicals which are themselves optionally substituted; or a morpholino radical, or pyrrolidino radical, it being understood that, in the above, the adjective "lower" applied to an organic radical means that this radical contains at most 6 carbon atoms.

2. A compound according to claim 1, in which:

n and R have the same meaning as in claim 1, and

R' represents the dimethylamino radical, an alkyl radical containing from 1 to 3 carbon atoms and optionally substituted by one or more halogens, or a, morpholino radical, or pyrrolidino radical.

3. A pesticidal composition for agricultural use, in combating phytopathogenic fungi, which comprises an effective amount of a compound according to claim 1 as the active ingredient, and an inert carrier or diluent.

4. A composition according to claim 3, which comprises, in addition to the active ingredient, an inert carrier and/or a surface-active agent which can be used in agriculture.

5. A composition according to claim 4, which comprises from 0.001% to 95% by weight of active ingredient and from 0 to 20% by weight of surface-active agent.

6. A process for the treatment of plants to combat phytopathogenic fungi, which consists in applying, to these plants, a fungicidally effective amount of a compound according to claim 1.

* * * * *